United States Patent [19]
Greenwald et al.

[11] Patent Number: 6,011,042
[45] Date of Patent: Jan. 4, 2000

[54] ACYL POLYMERIC DERIVATIVES OF AROMATIC HYDROXYL-CONTAINING COMPOUNDS

[75] Inventors: Richard B. Greenwald, Somerset; Annapurna Pendri, Matawan; Yun H. Choe, Piscataway, all of N.J.

[73] Assignee: Enzon, Inc., Piscataway, N.J.

[21] Appl. No.: 08/948,872

[22] Filed: Oct. 10, 1997

[51] Int. Cl.[7] .......................... A61K 31/33; C07D 491/22
[52] U.S. Cl. .............................. 514/283; 546/48; 560/19; 536/1.11
[58] Field of Search ............................. 514/283, 23, 540; 546/48; 560/19; 536/1.11

[56] References Cited

U.S. PATENT DOCUMENTS

| | | | |
|---|---|---|---|
| 5,004,758 | 4/1991 | Boehm et al. | 514/283 |
| 5,489,589 | 2/1996 | Wittman et al. | 514/232.8 |
| 5,541,327 | 7/1996 | Danishefsky et al. | 546/48 |
| 5,646,159 | 7/1997 | Wall et al. | 514/279 |
| 5,648,506 | 7/1997 | Desai et al. | 549/510 |
| 5,650,234 | 7/1997 | Dolence et al. | 428/447 |
| 5,654,302 | 8/1997 | Chenard | 514/235.5 |
| 5,663,177 | 9/1997 | Berges et al. | 514/279 |
| 5,837,673 | 11/1998 | Tsujihara et al. | 514/2 |
| 5,840,900 | 11/1998 | Greenwald et al. | 546/48 |

OTHER PUBLICATIONS

Ouchi T. et al., Synthesis of 5–Flourouracil–Terminated monomethoxypoly(ethylene glycol)s, Their hydrolysis behavior, and Their Antitumor Activities, J. Macromol. Sci.–Chem, A24(9), pp. 1011–1032 (1987).

*Primary Examiner*—Alan L. Rotman
*Assistant Examiner*—Charanjit S. Aulakh
*Attorney, Agent, or Firm*—Roberts & Mercanti, L.L.P.

[57] ABSTRACT

The present invention is directed to conjugates such as polymeric prodrugs of aromatic, hydroxyl-containing compounds and methods of making and using the same. These polymeric prodrugs are preferably esters of hydroxyl-containing aromatic compounds and are formed by reacting a desired aromatic, hydroxyl-containing compound with a substantially non-antigenic polymer so as to produce a transport form having an ester linkage between the aromatic compound and the polymer. Preferred aromatic hydroxyl-containing compositions include 10- and 11-hydroxycamptothecin derivatives. Methods of treatment are also disclosed.

42 Claims, No Drawings

ACYL POLYMERIC DERIVATIVES OF AROMATIC HYDROXYL-CONTAINING COMPOUNDS

TECHNICAL FIELD

The present invention relates to water soluble prodrugs. In particular, the invention relates to relatively high molecular weight, water soluble, non-antigenic polymeric esters of aromatic, hydroxyl-containing compounds such as camptothecin analogs.

BACKGROUND OF THE INVENTION

Over the years, several methods of administering biologically-effective materials to mammals have been proposed. Many medicinal agents are available as water-soluble salts and can be included in pharmaceutical formulations relatively easily. Problems arise when the desired medicinal agent is either insoluble in aqueous fluids or is rapidly degraded in vivo. Alkaloids are often especially difficult to solubilize.

One way to solubilize medicinal agents is to include them as part of a soluble prodrug. Prodrugs include chemical derivatives of a biologically-active parent compound which, upon administration, eventually liberate the parent compound in vivo. Prodrugs allow the artisan to modify the onset and/or duration of action of an agent in vivo and can modify the transportation, distribution or solubility of a drug in the body. Furthermore, prodrug formulations often reduce the toxicity and/or otherwise overcome difficulties encountered when administering pharmaceutical preparations. Typical examples of prodrugs include organic phosphates or esters of alcohols or thioalcohols. See *Remington's Pharmaceutical Sciences*, 16th Ed., A. Osol, Ed. (1980), the disclosure of which is incorporated by reference herein.

Prodrugs are often biologically inert or substantially inactive forms of the parent or active compound. The rate of release of the active drug, i.e. the rate of hydrolysis, is influenced by several factors but especially by the type of bond joining the parent drug to the modifier. Care must be taken to avoid preparing prodrugs which are eliminated through the kidney or reticular endothelial system, etc. before a sufficient amount of hydrolysis of the parent compound occurs. By incorporating a polymer as part of the prodrug system, one can increase the circulating life of the drug. However, it has been determined that when only one or two polymers of less than about 10,000 daltons are conjugated to certain biologically active substances such as alkaloids compounds, the resulting conjugates are rapidly eliminated in vivo especially if a somewhat hydrolysis-resistant linkage is used. In fact, such conjugates are so rapidly cleared from the body that even if a hydrolysis-prone ester linkage is used, not enough of the parent molecule is regenerated in vivo.

Camptothecin, related analogs and other aromatic-based biologically active compounds which are often poorly water soluble are examples of substances which would benefit from prodrug technology. A brief overview of some previous work in the field is presented below.

Ohya, et al., J. *Bioactive and Compatible Polymers* Vol. 10 January, 1995, 51–66, disclose doxorubicin-PEG conjugates which are prepared by linking the two substituents via various linkages including esters. The molecular weight of the PEG used, however, is only about 5,000 at most. Thus, the in vivo benefits are not expected to be realized because the conjugates are substantially excreted prior to sufficient linkage hydrolysis.

U.S. Pat. No. 4,943,579 discloses certain simple 20(S)-camptothecin amino acid esters in their salt forms as water soluble prodrugs. The reference does not, however, disclose using an amino acid as part of a linkage which would attach the alkaloid to a relatively high molecular weight polymer in order to form a prodrug or attaching the prodrug system at other locations. As evidenced by the data provided in Table 2 of the '579 patent, hydrolysis is rapid. Consequently, at physiologic pH, the insoluble base is rapidly generated after injection, binds to proteins and is quickly eliminated from the body before therapeutic effect can be achieved. A related effort was directed to developing a water-soluble camptothecin sodium salt. Unfortunately, the water-soluble sodium salt of camptothecin remained too toxic for clinical application (Gottlieb et al,. 1970 *Cancer Chemother, Rep.* 54, 461; Moertel et al,. 1972 ibid, 56, 95; Gottlieb et al., 1972 ibid, 56, 103).

Commonly-assigned PCT application WO96/23794 discloses inter alia 20-(S) camptothecin-polymeric esters. Additional research was conducted to determine whether useful prodrugs can be formed without including the 20-OH in view of the need to address concerns that for camptothecin, optimal activity requires an unsubstituted 20-hydroxyl position. For example, Well et al., in *Ann Review of Pharm Tox* 17:177, (1977), opined that the 20-OH must be unsubstituted in derivatives of 10-hydroxycamptothecin in order to retain the camptothecin structure and optimal anticancer/antitumor activity.

Acylation of simple aromatic hydroxyl groups is generally easily accomplished with simple acid chlorides or anhydrides in the presence of a base. However, selective acylations of aromatic hydroxyls with functionalized non-antigenic polymers such as acid chloride or N-hydroxysuccinimide esters of polyalkylene oxides such as PEG are often low yielding in spite of using various coupling reagents such as DIPC, DCC, Mukaiyama reagent, etc. and different bases such as pyridine, $Et_3N$, DMAP, $K_2CO_3$. Alternative synthesis techniques are desirable for those in the field of prodrugs.

Thus, there continues to be a need to provide additional technologies for forming prodrugs of not only camptothecin and related analogs but also other biologically important aromatic hydroxyl-containing compounds. In many cases, it would be advantageous to provide the artisan with alternative points for attaching the carrier so as to optimize biological effect. Furthermore, it would be desirable to provide additional techniques to address the problems of excessively fast or slow hydrolysis of the polymer from the parent drug and excessively rapid clearance of the prodrug from the body at physiological pH.

The present invention addresses the shortcomings described above.

SUMMARY THE INVENTION

The present invention addresses the shortcomings described above as well as providing additional advantages and features beyond chemotherapy of cancer or tumor conditions. In one aspect of the invention, compositions of Formula (I) are provided:

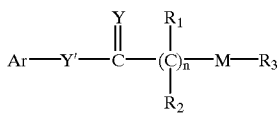

(I)

wherein:
  Ar is a residue of an aromatic, hydroxyl-containing compound;
  M is X or Q; where
    X is an electron withdrawing group; and
    Q is a moiety containing a free electron pair positioned three to six atoms from Y';
  Y and Y' are independently O or S;
  (n) is zero or a positive integer, preferably from about 1 to about 12;
  $R_1$ and $R_2$ are independently selected from the group consisting of H, $C_{1-6}$ alkyls, substituted alkyls, branched alkyls, aryls, substituted aryls, aralkyls, heteroalkyls, substituted heteroalkyls and substituted $C_{1-6}$ alkyls; and
  $R_3$ is a substantially non-antigenic polymer.

In one preferred embodiment, $R_3$ of (I) also includes a capping group off of oxygen Z, and Z may be one of H, $C_{1-6}$alkyl moieties, a dialkyl acyl urea alkyl, carboxy alkyls or

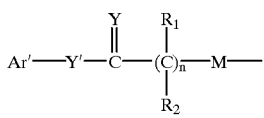

(II)

where Ar' is the same as Ar or a different residue of an aromatic hydroxyl-containing compound, hydrogen or a biologically active compound residue, and Y, Y', $R_1$, $R_2$, M and n are the same as that set forth above.

In formula (I), Ar is a residue of any aromatic, hydroxyl-containing compound for which one or more of improved aqueous solubility, decreased antigenicity, prodrug and/or controlled release delivery is desired. In certain preferred aspects, Ar is a residue of a biologically active compound such as a 10- or 11-hydroxycamptothecin or a 10,11-dihydroxycamptothecin analog. For purposes of the present invention, the term "residue" shall be understood to mean that portion of a biologically active compound which remains after it has undergone a substitution reaction in which the prodrug carrier portion has been attached.

In a preferred aspect of the invention, the aromatic, hydroxyl-containing compound is a biologically active compound that is suitable for medicinal or diagnostic use in the treatment of animals, e.g., mammals, including humans, for conditions for which such treatment is desired. In a more preferred aspect of the invention, the aromatic, hydroxyl-containing compound is an anticancer agent, such as the camptothecin compounds, as well as their related analogs and derivatives thereof When Ar and/or Ar' is a residue of medicinal or therapeutic agent, the polymeric ester thereof is referred to herein as a "prodrug".

Prodrugs according to the invention also include a water-soluble, substantially non-antigenic polymer (as $R_3$), preferably of relatively high molecular weight. Such non-antigenic polymers include, for example, a polyalkylene oxide such as polyethylene glycol, or alternatively, dextran, polyvinyl alcohols, carbohydrate-based polymers, hydroxypropylmethacrylate (HPMA), etc., and the like. Preferably, the non-antigenic polymer is a polyalkylene oxide polymer. In particular, $R_3$ is preferably a polyethylene glycol and has a molecular weight of at least about 20,000.

The prodrugs of the present invention are thus mono- and bis-polymer-based prodrugs where one or more active compound is attached to the water-soluble polymer, preferably via a hydrolyzable linkage such as a suitably activated ester linkage.

For purposes of the present invention, the term "alkyl" shall be understood to include straight, branched, substituted $C_{1-12}$ alkyls, $C_{5-8}$ cycloalkyls or substituted cycloalkyls, etc.

One of the chief advantages of the prodrug compounds of the present invention is that the prodrugs achieve a preferable balance between the rate of linkage hydrolysis and the rate of clearance of prodrug from the body. The linkage between the polymer and the parent compound as described above, hydrolyzes at a rate which allows a sufficient amount of the parent molecule to be released at the site of action, in vivo before clearance of the prodrug from the plasma or body.

Methods of making and using the compositions described herein are also provided.

DETAILED DESCRIPTION OF THE INVENTION

A. DERIVATIVES OF AROMATIC, HYDROXYL-CONTAINING COMPOUNDS

In one aspect of the invention, there are provided compounds of formula (I):

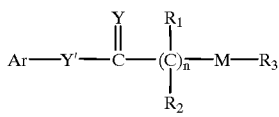

(I)

wherein:
  Ar is a residue of an aromatic, hydroxyl-containing compound;
  M is X or Q; where
    X is an electron withdrawing group; and
    Q is a moiety containing a free electron pair positioned three to six atoms from Y';
  Y and Y' are independently O or S;
  (n) is zero or a positive integer, preferably from about 1 to about 12;
  $R_1$ and $R_2$ are independently selected from the group consisting of H, $C_{1-6}$ alkyls including branched alkyls, aryls such as phenyl, substituted aryls such as p-chlorophenyl, aralkyls such as benzyl, heteroalkyls such as 3-pyridylmethyl, substituted heteroalkyls such as 2-thienyl alkyls and substituted $C_{1-6}$ alkyls such as haloalkyls; and
  $R_3$ is a substantially non-antigenic polymer which may be further substituted with Z described below.

B. POLYMERIC ESTERS OF AROMATIC, HYDROXYL-CONTAINING COMPOUNDS

In some preferred aspects, the present invention includes polymeric conjugates of aromatic hydroxyl-containing compounds. In preferred aspects, the conjugates advantageously contain hydrolyzable ester linkages between the polymer portion and the residue(s) of the aromatic hydroxyl-containing compound. These linkages are selected to hydrolyze in vivo at a rate which generates sufficient amounts of the parent compound within a suitable time after administration. The term "sufficient amounts" for purposes of the present invention shall mean an amount which achieves a desired effect. In alternative aspects where more hydrolysis-resistant linkages such as carbamates or carbonates are employed, the conjugates, in some embodiments, where higher molecular weight compounds are employed, prodrugs demonstrate improved targeting and accumulation in tumor areas where local enzymes can accelerate the hydrolysis of the transport or carrier portion and thus regenerate the parent compound.

In preferred aspects of the invention, $R_3$ includes a capping group off of oxygen Z which can be one of H, $C_{1-6}$ alkyl, dialkyl acyl urea alkyl, carboxyalkyl or

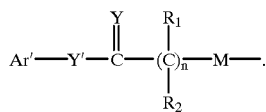

where (n), M, $R_1$, $R_2$, Y and Y' are as defined above and Ar' is the same as Ar, H, a different residue of an aromatic, hydroxyl-containing compound or another biologically active compound residue. The bis-compounds, therefore, have the formula (I')

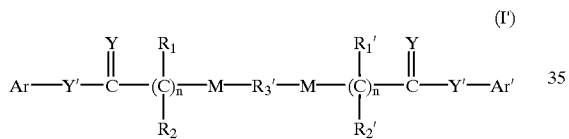

where $R_3'$ is a bifunctional linker moiety, such as the residue of $R_3$ as a result of the bis portion of the compound being present; and $R_1'$ and $R_2'$ are the same as $R_1$ and $R_2$ or another member of the group defined above for $R_1$ and $R_2$ and all other variables are the same as set forth above.

Ar and/or Ar', provide the compounds of the invention with utility in various industries, including the pharmaceutical, agriculture (e.g., animal husbandry, veterinary medicine, crop cultivation, and related fields) and/or as a diagnostic. The artisan will appreciate that such compounds may find use in additional art areas as well.

C. THE PRODRUG LINKAGE

1. The Electron Withdrawing Group X

Within the formula (I) described above, X is designated as an electron withdrawing group. In particular, X can be selected from moieties such as O, N($R_1$), S, SO and $SO_2$ where $R_1$ is as defined above, i.e. H, $C_{1-6}$ alkyls, branched alkyls, aryls, substituted aryls, $C_{1-6}$ alkyl aralkyls, heteroalkyls, substituted heteroalkyls or substituted $C_{1-6}$ alkyls such as carboxyalkyls, aminoalkyls, dialkylaminos, hydroxyalkyls or mercaptoalkyls, to name but a few. Preferably, however, when X is N($R_1$), $R_1$ is H, a $C_{1-6}$ alkyl such as methyl or ethyl or substituted $C_{1-6}$ alkyl. It is preferred that X is either O or N($R_1$).

For purposes of the present invention when (n) is 1 in Formulas (I) and (II), X is preferably a moiety which gives a substituted acetic acid with a pKa of less than about 4.0 upon hydrolysis of the prodrug ester. The moieties selected for X within the formula promote relatively rapid hydrolysis because of the low pKa of the resulting substituted acetic acid formed upon breakdown of the prodrug.

2. Q Portion of the Linker

When M is Q, the substantially non-antigenic polymer, $R_3$, is preferably attached to Q via a heteroatom such as oxygen. Q is a moiety containing a free electron pair positioned three to six atoms from Y' as shown below in Figure (III)

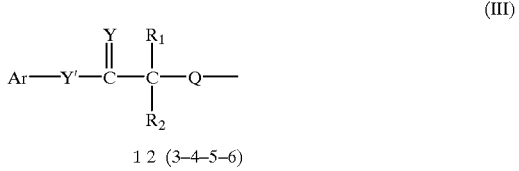

where $R_{1-2}$ are the same as that set forth above.

In a preferred embodiment, the free electron pair is five atoms from Y'. Q can be selected from the non-limiting list of $C_{2-4}$ alkyls or cycloalkyls, aryls or aralkyl groups substituted with a member of the group consisting of O, S and $NR_1$, wherein $R_1$ is the same as that set forth above. The free electron pair can be anywhere along the Q moiety as long as the defined spacing between the free electron pair and Y' is maintained.

Some particularly preferred moieties for Q include:

—NH—C(O) and ortho-substituted phenyl groups such as

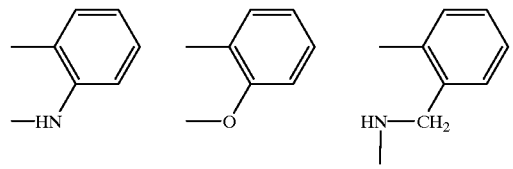

In these embodiments, the $R_3$ portion is attached to Q via $NR_1$, O, N, or S. Thus, Q, in formula (III), assists hydrolysis of the prodrug (ester) linkage by anchimeric assistance because the free electron pair moiety can generate a three- to six-membered, but preferably five-membered, ring by-product upon hydrolysis of the preferably ester linkage.

3. Hydrolysis and Parent Drug Regeneration

The prodrug compounds of the present invention are designed so that in plasma the $T_{1/2}$ circulation is greater than the $T_{1/2}$ hydrolysis, i.e. $T_{1/2}$ circulation $T_{1/2}$ hydrolysis.

The linkages included in the compounds have a $T_{1/2}$ hydrolysis in the plasma of the mammal being treated which is short enough to allow the parent compounds to be released prior to elimination. Some preferred compounds of the present invention, i.e. those in which (n) is 1, have plasma $T_{1/2}$ hydrolysis rates ranging from about 5 minutes to about 12 hours. Preferably, the compositions have a plasma $T_{1/2}$ hydrolysis ranging from about 0.5 to about 6 hours and most preferably from about 1 to about 4 hours.

D. SUBSTANTIALLY NON-ANTIGENIC POLYMERS

The prodrug compositions of the present invention include a water-soluble polymer, $R_3$. Suitable examples of such polymers include polyalkylene oxides such as polyethylene glycols which are also preferably substantially non-antigenic. The general formula for PEG and its derivatives, i.e. $Z'—O—(CH_2CH_2O)_x—(CH_2)_n—Z$, where (x) represents the degree of polymerization (i.e. 1–1800) or number of repeating units in the polymer chain and is dependent on the molecular weight of the polymer, (n) is zero or a positive integer, Z is a capping group off of oxygen as defined herein, i.e. an —H, carboxyalkyl or a $C_{1-6}$ alkyl and Z' is the same as Z or another Z moiety. Also useful are polypropylene glycols, branched PEG derivatives such as those described in commonly-assigned U.S. Pat. No. 5,643,575, "star-PEG's" and multi-armed PEG's such as those described in Shearwater Polymers, Inc. catalog "Polyethylene Glycol Derivatives 1997–1998". The disclosure of each is incorporated herein by reference. It will be understood that the water-soluble polymer will be functionalized for attachment to the linkage via M, X or Q herein. As an example, the PEG portion of the prodrugs can be the following non-limiting compoounds:

$—C(=Y)—(CH_2)_n—O—(CH_2CH_2O)_x—Z$,
$—C(=Y)—Y—(CH_2)_n—O—(CH_2CH_2O)_x—Z$,
$—C(=Y)—NR_1—(CH_2)_n—O—(CH_2CH_2O)_x—Z$,
$—CR_1R_2—(CH_2)_n—O—(CH_2CH_2O)_x—Z$.

where Y, Z, $R_1$, $R_2$, (n) and (x) are as defined above.

In particular, polyethylene glycols (PEG's), mono-activated, $C_{1-4}$ alkyl-terminated PAO's such as monomethyl-terminated polyethylene glycols (mPEG's) are preferred when mono-substituted polymers are desired; bis-activated polyethylene oxides are preferred when disubstituted prodrugs are desired. In order to provide the desired hydrolyzable linkage, mono- or di-acid activated polymers such as PEG acids or PEG diacids are used. Suitable PAO acids can be synthesized by first converting mPEG-OH to an ethyl ester followed by saponification. See also Gehrhardt, H., et al. Polymer Bulletin 18: 487 (1987) and Veronese, F. M., et al., J. Controlled Release 10; 145 (1989). Alternatively, the PAO-acid can be synthesized by converting mPEG-OH into a t-butyl ester followed by acid cleavage. See, for example, commonly assigned U.S. Pat. No. 5,605,976. The disclosures of each of the foregoing are incorporated by reference herein.

Although PAO's and PEG's can vary substantially in molecular weight, polymers having molecular weight ranges of at least 20,000 are preferred. Polymers ranging from about 20,000 to about 80,000 are usually selected for the purposes of the present invention. Molecular weights of from about 25,000 to about 45,000 are preferred and 30,000 to about 42,000 are particularly preferred. The molecular weight of the polymer selected for inclusion in the prodrug must be sufficient so as to provide sufficient circulation of the prodrug during hydrolysis of the linker.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

As an alternative to PAO-based polymers, effectively non-antigenic materials such as dextran, polyvinyl alcohols, carbohydrate-based polymers, hydroxypropylmethacrylamide (HPMA), and copolymers thereof etc. and the like can be used if the same type of ester activation is employed as described herein for PAO's such as PEG, i.e. conversion of alcohol to a 2-alkoxy acid. Those of ordinary skill in the art will realize that the foregoing list is merely illustrative and that all polymeric materials having the qualities described herein are contemplated. For purposes of the present invention, "effectively non-antigenic" means all polymeric materials understood in the art as being nontoxic and not eliciting an appreciable immune response in mammals.

As mentioned above, certain prodrugs of the present invention include two equivalents of aromatic compound per equivalent of (polymer) linker. As such, preferred bifunctional linking compounds such as substantially non-antigenic polymers will be functionalized to form the bis-prodrugs. One preferred activated polymer linker is represented below as formula (IV):

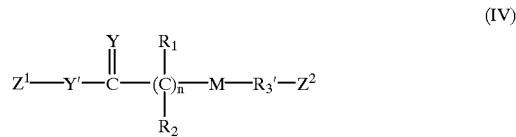

(IV)

wherein:

M, $R_{1-2}$, $R_3'$, Y, Y' and n are the same as that set forth above;

$Z^1$ and $Z^2$ are independently $CO_2R_4$, $OR_5$, $COR_6$, H, or a $C_{1-4}$ alkyl, branched or substituted alkyl $R_4$ is an N-succinimidyl, an N-benzotriazolyl, or other acid activating group;

$R_5$ is $R_1$ or C(=O)-halogen, para nitrophenyl carbonate, imidazolyl carbonate, or N-hydroxysuccinimidyl carbonate; and $R_6$ is thiazolidine thione, imidazole or an acid activating group.

In this aspect of the invention, it will be understood that if one of $Z^1$ and $Z^2$ is a capping group, a monofunctional polymer is formed. Bifunctional linkers require that neither $Z^1$ nor $Z^2$ be a capping group. Preferably, Y and Y' are both preferably O, and $R_3'$ is a substantially non-antigenic polymer residue having a molecular weight of about 20,000 or greater. Although, the prodrugs of the present invention can be formed using any of the substantially non-antigenic polymers described herein, the following polyalkylene oxide PEG-conjugated amino acids or PEG-acids and PEG-diacids are especially preferred for use in formation of the prodrug:

a) $HO_2C(CH_2)_nS—(CH_2)_2—O—PEG—O—(CH_2)_2—S—(CH_2)_nCO_2H$;

b) $HO_2C—CH_2—O—PEG—O—CH_2—CO_2H$;

c)

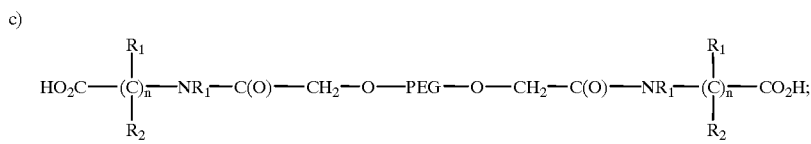

d) $CH_3—O—PEG—O—(CH_2)_n—CO_2H$;

where $R_1$, $R_2$ and (n) are the same as that defined above.

It will be clear from the foregoing that other polyalkylene oxide derivatives of the foregoing are also contemplated, such as the polypropylene glycol acids, POG acids, etc.

E. PRODRUG CANDIDATES

It is noted that parent compounds suitable for incorporation into the prodrug compositions of the invention, may themselves be substances/compounds which are not active after hydrolytic release from the linked composition, but which will become active after undergoing a further chemical process/reaction. For example, an anticancer drug that is delivered to the bloodstream by hydrolysis of the compositions of the invention, may remain inactive until entering a cancer or tumor cell, whereupon it is activated by the cancer or tumor cell chemistry, e.g., by an enzymatic reaction unique to that cell.

Preferred biologically active moieties which are candidates for inclusion with the prodrug carriers described herein are generally referred to as aromatic, hydroxyl-containing compounds. Such compounds will be apparent to those of ordinary skill as those compounds having an available hydroxyl on one of the aromatic portions of the compound such as a phenolic-OH or quinolone-OH, quinoline-OH, pyridone-OH, N-hydroxypyridone-OH, other heteroaromatic-OH containing compounds. A non-limiting list of such compounds include certain camptothecin analogs (described in detail below) such as topotecan, SN-38, i.e. 7-ethyl-10-hydroxycamptothecin, 7-alkyl-10-hydroxycamptothecins; etoposide; nitrogen mustard derivatives such as parahydroxyaniline mustard, tetracyclic pharmaceuticals such as tetracyclines, doxycycline, anthracyclines, and related compounds; quinolone antibiotics, combretastatin and derivatives thereof. Still others include biologically active compounds which contain the required aromatic hydroxyl such as other anti-tumor agents, cardiovascular agents, anti-neoplastics, anti-infectives, anti-fungals, anti-anxiety agents, gastrointestinal agents, central nervous system-activating agents, analgesics, fertility or contraceptive agents, anti-inflammatory agents, steroidal agents, anti-urecemic agents, cardiovascular agents, vasodilating agents, vasoconstricting agents and the like are also contemplated. The foregoing list is meant to be illustrative and not limiting for the compounds which can be modified. Those of ordinary skill will realize that other such compounds can be similarly modified without undue experimentation. It is to be understood that those biologically active materials not specifically mentioned but having suitable ester-forming groups are also intended and are within the scope of the present invention.

The only limitations on the types of aromatic molecules suitable for inclusion herein is that there is available at least one aromatic OH-containing position which can react and link with a carrier portion and that there is not substantial loss of bioactivity after the prodrug releases and regenerates the parent compound, i.e. Ar—OH, in vivo.

Camptothecin and Related Topoisomerase Inhibitors

Camptothecin is a water-insoluble cytotoxic alkaloid produced by *camptoteca accuminata* trees indigenous to China and *nothapodytes foetida* trees indigenous to India. Camptothecin and related compounds and analogs are also known to be potential anticancer or antitumor agents and have been shown to exhibit these activities in vitro and in vivo in laboratory animals. Camptothecin and certain related analogues share the structure:

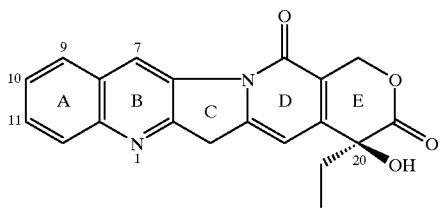

From this core structure, several known analogs have been prepared. For example, the A ring in either or both of the 10- and 11-positions can be substituted with an OH. The A ring can also be substituted with a straight or branched $C_{1-30}$ alkyl or $C_{1-17}$ alkoxy, optionally linked to the ring by a heteroatom i.e. —O or S. The B ring can be substituted in the 7-position with a straight or branched $C_{1-30}$ alkyl, $C_{5-8}$ cycloakyl, $C_{1-30}$ alkoxy, phenyl alkyl, etc., alkyl carbamate, alkyl carbazides, phenyl hydrazine derivatives, etc. Other substitutions are possible in the C, D and E rings. See, for example, U.S. Pat. Nos. 5,004,758; 4,943,579; Re 32,518, the contents of which are incorporated herein by reference. Preferred camptothecin derivatives for use herein include the 10-hydroxycamptothecin such as topotecan, 11-hydroxycamptothecin and/or the 10,11-dihydroxycamptothecin derivatives. The prodrug carrier portion is thus attached via a substitution reaction such as that described below involving one or more of the aromatic OH groups. As the artisan will appreciate, the 10-hydroxycamptothecin, 11-hydroxycamptothecin and the 10,11-dihydroxycamtothecin analogs occur naturally as one of the minor components in *C. Acuminata* and its relatives. Additional substitutions to these compounds, i.e. 7-alkyl-, 7-substituted alkyl-, 7-amino-, 7-aminoalkyl-, 7-aralkyl-, 9-alkyl-, 9-aralkyl-camptothecin etc. derviatives can be made using known synthetic techniques without undue experimentation. Structurally, these compounds are all A-ring oxygenated camptotheca alkaloids as shown below.

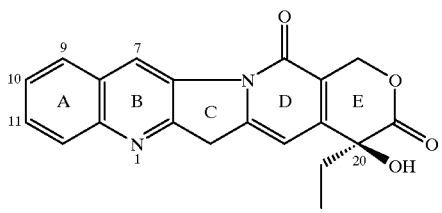

In the structure shown above, $R_7$ is one of $NO_2$, $NH_2$, $N_3$, hydrogen, halogen (F, Cl, Br, I), COOH, OH, O—$C_{1-8}$ alkyl, SH, S—$C_{1-3}$ alkyl, CN, $CH_2NH_2$, NH—$C_{1-3}$ alkyl, $CH_2$—NH—$C_{1-3}$ alkyl, N($C_{1-3}$ alkyl)$_2$, $CH_2N(C_{1-3}$alkyl), O—, NH— and S—$CH_2CH_2N(CH_2CH_2OH)_2$, O—, NH— and S—$CH_2CH_2CH_2N(CH_2CH_2OH)_2$, O—, NH— and S—$CH_2CH_2N(CH_2CH_2CH_2OH)_2$, O—, NH— and S—$CH_2CH_2CH_2N(CH_2CH_2CH_2OH)_2$, O—, NH— and S—$CH_2CH_2N(C_{1-3}$ alkyl)$_2$, O—, NH— and S—$CH_2CH_2CH_2N(C_{1-3}$ alkyl)$_2$, CHO or $C_{1-3}$ alkyl. Preferred compounds are those in which $R_7$ is halogen, nitro or amino.

$R_8$ in the structure (IV) shown above is H, $C_{1-8}$ alkyl, or $CH_2NR_9R_{10}$ where (a) $R_9$ and $R_{10}$ are, independently, hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy-$C_{1-6}$ alkyl;

(b) $R_9$ is hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy, $C_{1-6}$ alkyl, $C_{1-6}$ alkoxy or $C_{1-4}$ alkoxy-$C_{1-6}$ alkyl and $R_{10}$ is —$COR_{11}$ where $R_{11}$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy, $C_{1-6}$ alkoxy-$C_{1-6}$ alkyl; or (c) $R_9$ and $R_{10}$ taken together with the nitrogen atom to which they are attached form a saturated 3–7 membered heterocyclic ring which may contain a O, S or $NR_{12}$ group, where $R_{12}$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$alkylamino, perhalo-$C_{1-6}$ alkyl, hydroxy-$C_{1-6}$ alkyl, $C_{1-6}$ alkoxy, $C_{1-6}$ alkoxy-$C_{1-6}$ alkyl and —$COR_{13}$ where $R_{13}$ is hydrogen, $C_{1-6}$ alkyl perhalo-$C_{1-6}$ alkyl, $C_{1-6}$ alkoxy, aryl, and aryl substituted with one or more of $C_{1-6}$ alkyl, perhalo-$C_{1-6}$ alkyl, hydroxy-$C_{1-6}$ alkyl, or $C_{1-6}$ alkoxy-$C_{1-6}$ alkyl groups.

Preferred aryl groups are phenyl and naphthyl. Suitable heterocyclic rings when $R_9$ and $R_{10}$ are taken together with the nitrogen atom to which they are attached include: aziridine, azetidine, pyrrolidine, piperidine, hexamethylenimine, imidazolidine, pyrazolidine, isoxazolidine, piperazine, N-methylpiperazine, tetrahydroazepine, N-methyl-tetrahydroazepine, thiazolidine, etc.

After conjugation, the remaining camptothecin analog is referred to as the residue of the unconjugated compound. It will be understood that other aromatic compounds containing the requisite OH groups will also be residues and that the attachment of the carrier portion is effected in a similar manner without undue experimentation. Reference to camptothecin analogs herein has been made for purposes of illustration and not limitation.

Formation of a monoester camptothecin prodrug can be accomplished by reacting one or more equivalents of a suitably activated polymer with, for example, one equivalent of a 10- or 11-hydroxycamptothecin under conditions which are sufficient to effectively cause the 10- or 11-OH to undergo a substitution reaction with the activated polymeric carrier portion of the prodrug and form a linkage. Diesters are similarly prepared by reacting at least about 2 and preferably greater equivalents of the camptothecin derivative with a suitably prepared PAO or other non-antigenic polymer derivative diacid.

The resultant prodrugs have one of the formulae:

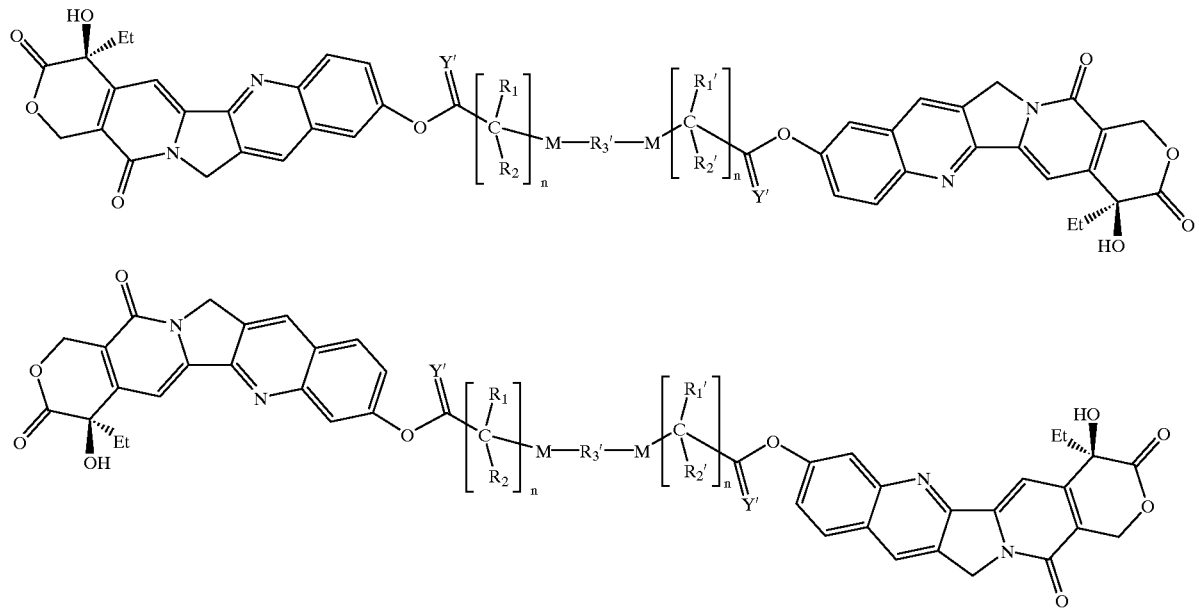

D. SYNTHESIS OF PRODRUGS

Synthesis of prodrugs is set forth in the Examples. Generally, however, the prodrugs of the invention i.e.

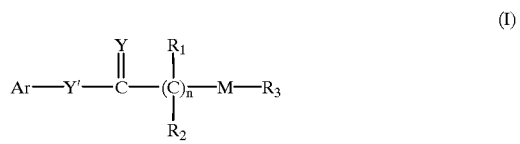

(I)

are prepared by reacting at least one equivalent of an aromatic, hydroxyl-containing compound designated herein as Ar-OH with an acid derivative of a linking compound $R'_3$ such as a substantially non-antigenic polymer residue of formula (IV):

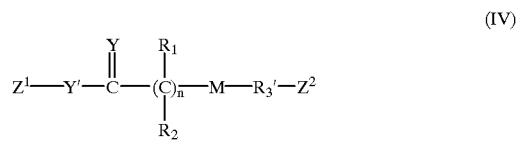

(IV)

wherein:

M, $R_{1-2}$, $R_3'$, Y, Y', $Z^1$ and $Z^2$ and n are the same as that set forth above except that $Z^1$ and $Z^2$ are not capping groups.

In an alternative embodiment, such as when $R_4$ or $R_5$ or $R_6$ is other than carboxylic acid, i.e. they are N-succinimidyl, N-benzotriazolyl, N-thiazolidyl thione, imidazolyl, C(=O)-halogen, para nitrophenyl carbonate, imidazolyl carbonate, or N-hydroxysuccinimidyl carbonate, the synthesis is achieved by reacting Ar—OH with a compound of Formula (IV) and an acid chloride derivative of phenyl phosphonic acid such as phenyl dichlorophosphate or other aryl dihalophosphate under mild conditions. As an alternative to the acid chloride derivative of phenyl phosphonic acid, a dialkylaminophosphoramidic dihalide can be used.

Examples of suitable aryl dihalophosphates agents include phenyl dichlorophosphate, which is available from Sigma Chemical, or can be synthesized using known techniques. Other aryl dihalophosphates are similarly obtained. Aryl dihalophosphates are preferred for synthesis of 10- or 11-hydroxycamptothecin prodrugs. The resulting conjugated prodrug composition is then recovered or isolated using techniques known to those of ordinary skill, i.e. filtered, recrystallized.

Preferably the substituents are reacted in an inert solvent such as methylene chloride, chloroform, toluene or DMF or mixtures thereof The reaction also preferably is conducted in the presence of a base, such as dimethylaminopyridine, diisopropyl ethylamine, pyridine (preferred), triethylamine, etc. to neutralize any acids generated and at a temperature from 0° C. up to about 22° C. (room temperature).

In a preferred aspect, the synthesis methods provides polymer-based prodrugs having a circulation half-life greater than their in-vivo hydrolysis half-life.

An alternative synthesis route is provided in yet another aspect of the invention. The conjugate compositions are prepared by the steps of: (i). attaching a bifunctional spacer moiety such as glycine, l-alanine, and d-alanine or other amino acid derivatives to a substantially non-antigenic polymer (SNAP); (ii). reacting the SNAP-spacer moiety with biologically active aromatic moiety containing an available hydroxyl group in the presence of a coupling agent; and (iii). recovering the polymer-based prodrug. Preferably, the coupling agent is phenyl-dichlorophosphate. Alternatively, the coupling agent can be selected from materials such as 1,3-diisopropylcarbodiimide (DIPC), dialkyl carbodiimides, 2-halo-1-alkyl-pyridinium halides, 1-(3-dimethylaminopropyl)-3-ethyl carbodiimide (EDC), propane phosphonic acid cyclic anhydride (PPACA) and carbodiimide (CDI).

F. METHODS OF TREATMENT

Another aspect of the present invention provides methods of treatment for various medical conditions in mammals. The methods include administering to the mammal in need of such treatment, an effective amount of a composition of the invention, e.g., a polymeric ester-linked aromatic, medicament as described herein, such as a polymeric ester of a camptothecin, camptothecin derivative, camptothecin analog and/or a mixture thereof. For example, the composition includes a 10-hydroxy-camptothecin derivative, and/or a 11-hydroxycamptothecin derivative. The compositions are useful for, among other things, treating neoplastic disease, reducing tumor burden, preventing metastasis of neoplasms and preventing recurrences of tumor/neoplastic growths in mammals.

The amount of the composition, e.g., used as a prodrug, that is administered will depend upon the parent molecule included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. In general, polymeric ester derivatives of camptothecin and related compositions and nitrogen mustard derivatives are administered in amounts ranging from about 5 to about 500 mg/m$^2$ per day. The range set forth above is illustrative and those skilled in the art will determine the optimal dosing of the prodrug selected based on clinical experience and the treatment indication.

The compositions, including prodrugs, of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may also be by infusion into a body space or cavity, as well as by inhalation and/or intranasal routes. In preferred aspects of the invention, however, the prodrugs are parenterally administered to mammals in need thereof

G. EXAMPLES

The following examples serve to provide further appreciation of the invention but are not meant in any way to restrict the effective scope of the invention.

Example 1

10-POLY(ETHYLENE GLYCOL) ESTER OF CAMPTOTHECIN

A mixture of 1.0 g (0.025 mmol) of PEG dicarboxylic acid (40 kDa) and 35 mg (0.096 mmol) of 10-hydroxycamptothecin (Golden Bridge International, San Francisco, Calif.) in 30 mL of toluene was azeotroped by distillation of 15 mL of toluene. The mixture was cooled to room temperature and the solvent was removed by distillation in vacuo. 30 mL of anhydrous chloroform (Aldrich) was added to the mixture followed by addition of 1.0 mL (12.4 mmol) of pyridine and 0.15 mL (1.0 mmol) of phenyl dichlorophosphate (Aldrich) was added to the mixture. The reaction mixture was stirred at room temperature for 18 hours. The solution was washed with ice-cold 1 N HCl (25 mL×2), dried over anhydrous sodium sulfate, and concentrated under reduced pressure to give a light yellow solid. The crude product was recrystallized from 150 mL of 2-propanol to give a white solid as the final product (0.8918 g, 89% yield). The reaction is illustrated schematically below.

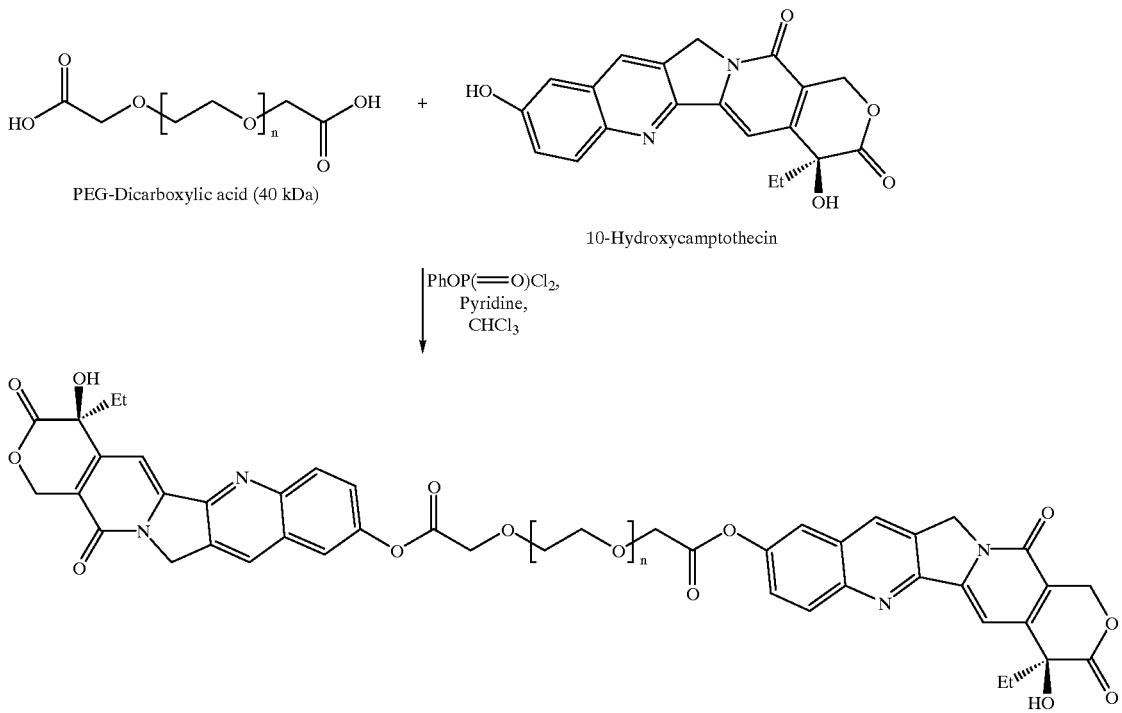

Analysis

UV absorbance assay was conducted as previously reported, Greenwald, R. B., et al., 1996, *J. Med. Chem.*, 39:424–431, the contents of which are incorporated herein by reference. The UV absorbance assay showed a 95% yield of 10-hydroxycamptothecin (1.8890 camptothecin equiv.) in the product. A qualitative ferric chloride test was conducted by adding 10% ferric chloride solution in methanol to the product and 10-hydroxycamptothecin on TLC. On TLC, the 10-hydroxycamptothecin showed a darker yellow edge on the spot and the pegylated 10-hydroxycamptothecin showed only yellow color from ferric chloride solution. This confirmed that the product showed no presence of phenolic OH.

The product was further characterized by HPLC, $^1$H NMR, and $^{13}$C NMR. $^1$H NMR (270 MHz, CDCl$_3$)δ 0.98 (t, J=11.2 Hz, H-18), 1.83 (q, J=8.6 Hz, H-19), 2.94 (s, PEG), 3.38–3.90 (bS, PEG), 4.53 (s, PEG-O-CH$_2$-CO$_2$-(20)-camptothecin), 5.31 (s, H-5), 5.19–5.69 (ABq, J=108.21, 27.06 Hz, H-17), 7.2 (d, J=11.21 Hz, H-11), 7.64 (s, H-9), 7.82 (s, H-14), 8.18 (d, J=11.88 Hz, H-12), 8.44 (s, H-7). $^{13}$C NMR (67.80 MHz, CDCl$_3$)δ 7.33, 31.10, 49.53, 65.65, 68.13, 70.03–70.97 (PEG), 77.92, 97.45, 118.24, 118.42, 125.05, 127.94, 128.85, 130.45, 130.78, 145.57, 146.35, 148.55, 149.64, 152.07, 156.97, 168.30, 172.98.

Example 2

11-POLY(ETHYLENE GLYCOL) ESTER OF 11-HYDROXYCAMPTOTHECIN

The process of Example 1 is repeated using 11-hydroxycamptothecin in place of the 10-hydroxycamptothecin. The title compound is recovered.

Example 3

10POLY(ETHYLENE GLYCOL) ESTER OF TOPOTECAN

The process of Example 1 is repeated using topotecan, in place of the 10-hydroxycamptothecin. The title compound is recovered.

Example 4

P-POLY(ETHYLENE GLYCOL) ESTER OF N,N-DI-2-CHLOROETHYLANILINE

A mixture of 1.0 g (0.025 mmol) of PEG dicarboxylic acid (40 kDa) in 30 mL of toluene was azeotroped by distillation of 15 mL of toluene. The solution was cooled to room temperature and the solvent was removed by distillation in vacuo. 20 mL of anhydrous methylene chloride was added to the residue followed by addition of 40 mg (0.15 mmol) of p-hydroxy-(N,N-di-2-chloroethyl)aniline hydrochloride (synthesized using a modified procedure of Edwards et al. Cytotoxic Compounds. Part XVII. o-, m-, and p-(Bis-2-chloroethylamino)phenol, p-[N-(2-Chloethyl)methylamino]phenol, N,N-Bis-2-chloroehyl-p-phenylenediamine, and N,N-Bis-2-chloroethyl-N-methyl-p-phenylenediamine as Sources of Biologically Active Carbamates. *JCS Perkin I*, (1973), 2397, the disclosure of which is incorporated herein by reference), 1.0 mL (12.4 mmol) of pyridine and 0.15 mL (1.0 mmol) of phenyl dichlorophosphate to the solution. The reaction mixture was stirred at room temperature for 18 hours. The solution was washed with ice-cold 1 N HCl (25 mL×2), dried over anhydrous sodium sulfate, and concentrated under reduced pressure to give a light green solid. The crude product was recrystallized from 2-propanol to give a white solid as the product (0.87 g, 87% yield). UV assay showed 2.03 equivalent of aromatic nitrogen mustard (100% coupling yield). $^1$H NMR (270 MHz, CDCl$_3$)δ 3.47–3.99 (PEG, 4×CH$_2$), 6.81 (d, J=8.2 Hz, Ar-H), 7.12 (d, J=8.2 Hz, Ar-H). $^{13}$C NMR (67.80 MHz, CDCl$_3$)δ 40.10, 53.35, 68.16–71.45 (PEG), 113.04, 121.66, 129.82, 143.27, 168.42.

The reaction is schematically represented below.

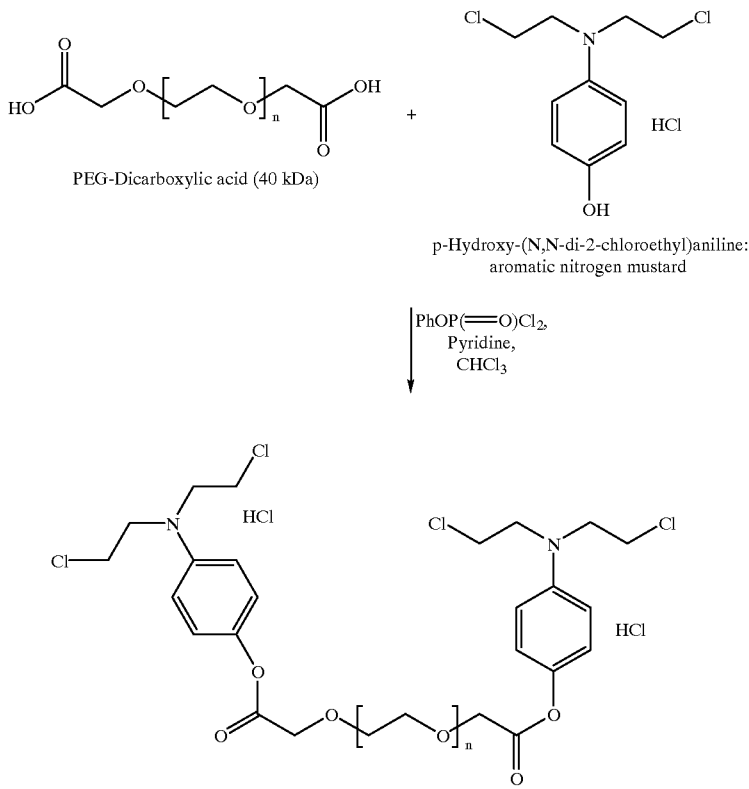

Example 5

10-POLY(ETHYLENE GLYCOL) ESTER OF 7-ETHYL-CAMPTOTHECIN

In this example, the process of Example 1 is repeated using 7-ethyl-10-hydroxycamptothecin. The title compound is recovered.

Example 6

POLY(ETHYLENE GLYCOL) AROMATIC ESTER OF ETOPOSIDE

1. From PEG Dicarboxylic Acid

A mixture of 1.0 g (0.025 mmol) of PEG dicarboxylic acid (40 kDa) in 30 mL of toluene was azeotroped by distillation of 15 mL of toluene. The solution was cooled to room temperature and the solvent was removed by distillation in vacuo. 20 mL of anhydrous methylene chloride was added to the residue followed by addition of 55 mg (0.093 mmol) of etoposide (purchased from Cormed, Ill.), 200 μL (1.68 mmol) of N,N-dimethylphosphoramidic dichloride (purchased from Fluka), 2.0 mL (14.3 mmol) of triethyl amine, and 20 mg (0.2 mmol) of 4-dimethylaminopyridine to the solution. The reaction mixture was stirred at room temperature overnight. The solution was washed with ice-cold 1 N HCl (25 mL×2), dried over anhydrous sodium sulfate, and concentrated under reduced pressure. The crude product was recrystallized from 2-propanol to give a white solid as the product (0.90 g, 90% yield). UV assay showed 1.74 equivalent of etoposide (87% coupling yield). $^{13}$C NMR (67.80 MHz, CDCl$_3$)δ 19.82, 37.90, 41.19, 44.03, 55.88, 56.21, 66.20, 67.24, 67.64, 67.82–73.11 (PEG), 73.24, 74.47, 99.15, 101.13, 101.99, 107.98, 108.53, 109.06, 110.05, 128.80, 132.38, 135.24, 138.12, 146.56, 147.47, 148.37, 151.28, 167.33, 173.74.

The reaction scheme is shown below along with that for method 2.

2. From PEG Thiazolidine-Thione

A mixture of 1.0 g (0.025 mmol) of PEG di Thiazolidine thione (40 kDa), 50 mg (0.085 mmol) of etoposide, and 50 mg (0.49 mol) of 4-dimethylaminopyridine in 20 mL of anhydrous dichloromethane was refluxed overnight. The reaction solution was cooled to room temperature and the solvent was removed in vacuo. The residue was recrystallized from 2-propanol to give 0.91 g (91% yield) of white solid as the product. UV assay showed 2.0 equivalent of etoposide (100% coupling yield). NMR data were consistent with the product prepared from the previous method.

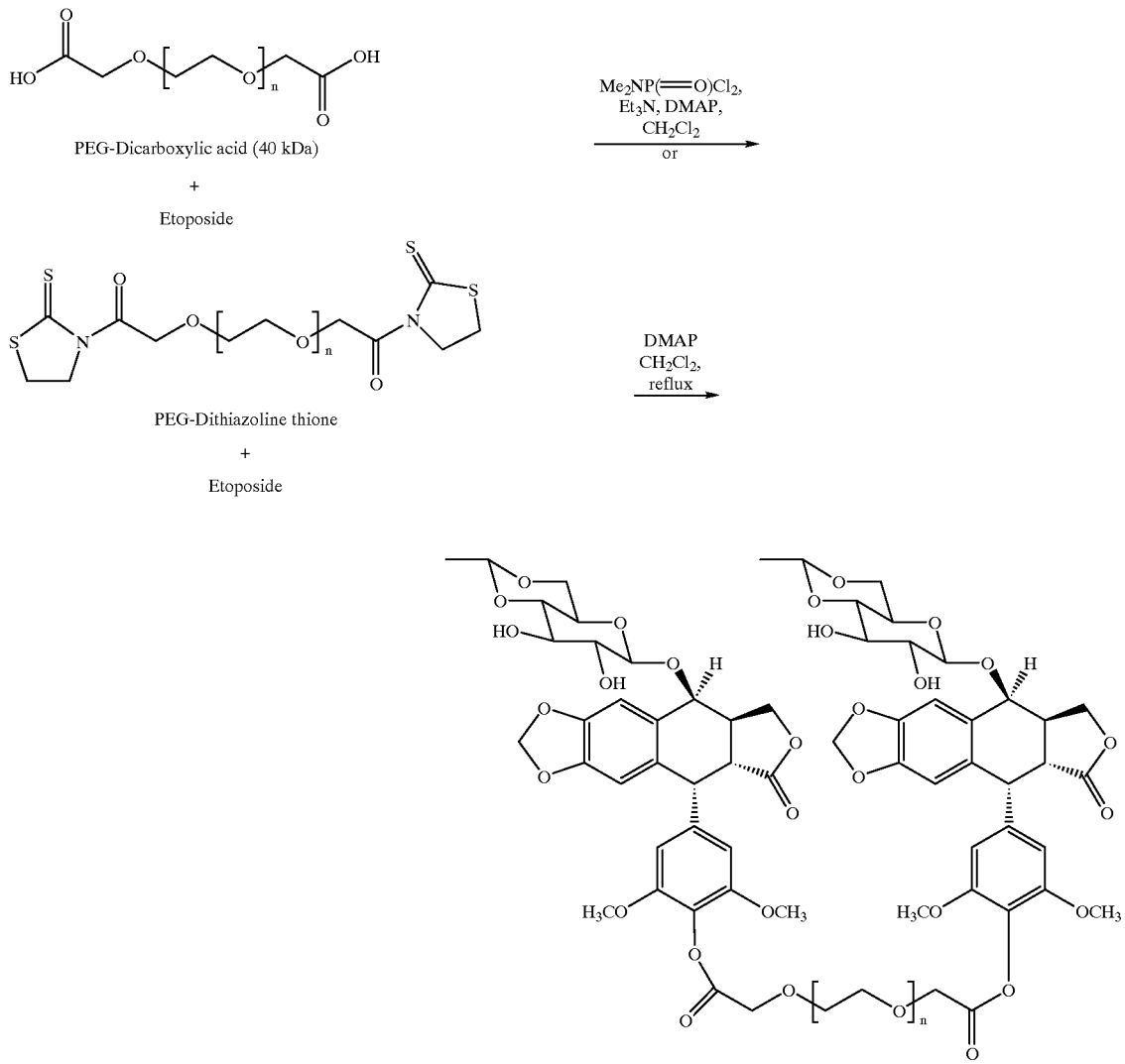

Example 7

10-N-METHYLAMINO POLY(ETHYLENE GLYCOL) CARBAMATE CAMPTOTHECIN

A mixture of 80 mg (0.22 mmol) of 10-hydroxycamptothecin, 110 mg (0.37 mmol) of triphosgene, 2 mL (0.014 mol) of triethylamine, and 1 mL (0.012 mol) of pyridine in anhydrous dichloromethane was stirred at room temperature for 2 hours. 2 g (0.05 mmol) of N,N-dimethyl-di-amino PEG (40 kDa) was azeotroped in 30 mL of toluene by refluxing with Dean-Stark apparatus for 2 hours and the solvent was evaporated in vacuo. 10-Chlorocarbonyloxy-camptothecin mixture was added to the residue followed by addition of 1 mL (0.012 mol) of pyridine and the mixture was stirred at room temperature overnight. The solution was washed with ice-cold 1 N HCl (25 mL×2), dried over anhydrous sodium sulfate, and concentrated under reduced pressure to give a light yellow solid. The crude product was recrystallized from 150 mL of 2-propanol to give a white solid as a product (1.6659 g, 83% yield). UV absorbance assay showed 1.0247 equivalent of 10-hydroxycamptothecin. The reaction scheme is shown below.

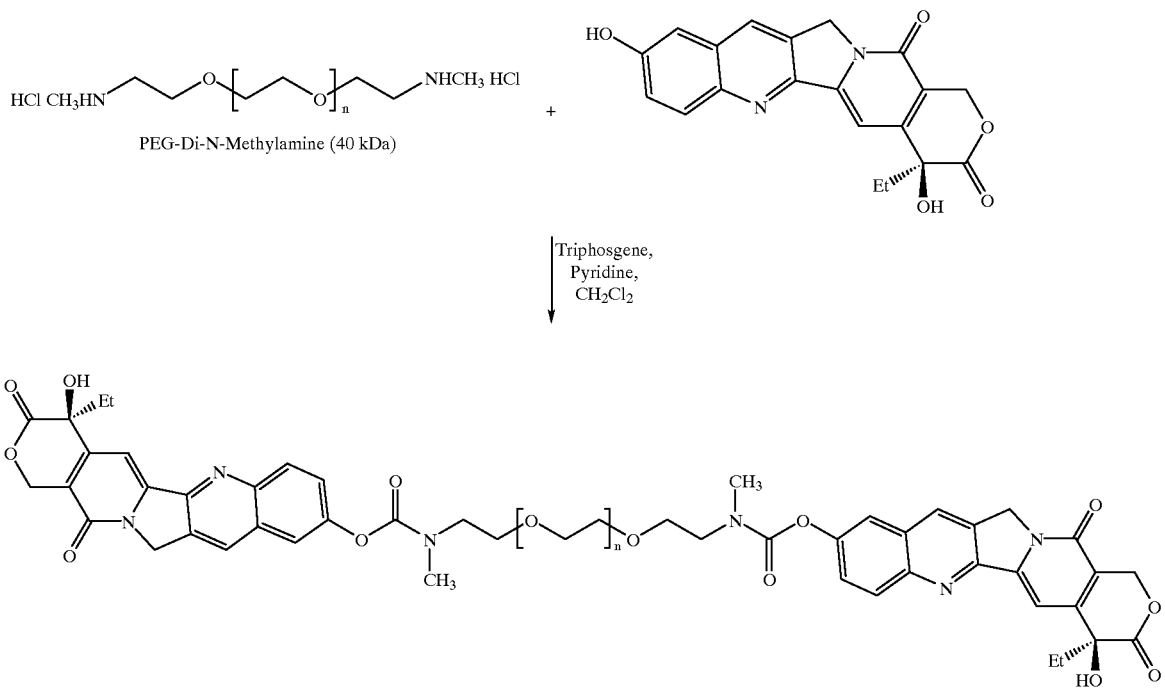

Example 8

10-POLY(ETHYLENE GLYCOL) CARBONATE CAMPTOTHECIN

A mixture of 40 mg (0.11 mmol) of 10-hydroxycamptothecin, 55 mg (0.19 mmol) of triphosgene, 2 mL (0.024 mol) of pyridine in 20 mL of anhydrous dichloromethane was stirred at room temperature for 2 hours. 1 g (0.025 mmol) of PEG diol (40 kDa) was azeotroped in 30 mL of toluene by refluxing with Dean-Stark apparatus for 2 hours and the solvent was evaporated in vacuo. 10-Chlorocarbonyloxycamptothecin solution was added to the residue and the mixture was stirred at room temperature overnight. The solution was washed with ice-cold 1 N HCl (25 mL×2), dried over anhydrous sodium sulfate, and concentrated under reduced pressure to give a light yellow solid. The crude product was recrystallized from 150 mL of 2-propanol to give a white solid as a product (0.80919 g, 81% yield). The reaction scheme is shown below.

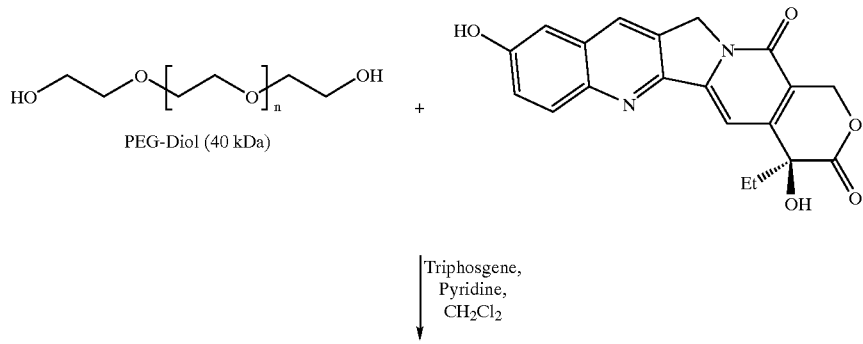

-continued

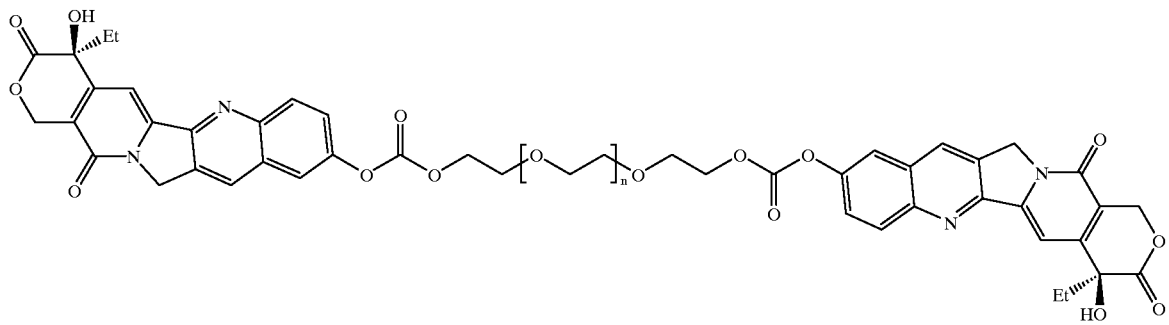

Example 9

IN VIVO STUDY

In this Example, the in vivo efficacy of 10-hydroxycamptothecin and the 10-poly(ethylene glycol) ester of camptothecin, prepared in accordance with Example 1, were evaluated using the P388/0 murine leukemia model. The P388/0 cell line was obtained from Southern Research Institute (Birmingham, Ala.) and grown in RPMI 1640 supplemented with 10% FBS. P388/0 cells were subcultured two times per week and log phase cultures (viability ≧95%) were used for all in vivo experiments. Female CD2F1 mice (Taconic Farms, Germantown, N.Y.) at 7–8 weeks of age were used for study. Following one week of acclimation, mice were implanted intraperitoneal (ip) with P388/0 cells ($5 \times 10^5$ cells/mouse) at designated day 0 (zero). The mice were randomly assigned to experimental groups (10–20 per group). Test materials (500 µl) were given daily [ipx5], twenty-four hours following the injection of P388/0 cells with survival monitored for 40–42 days. Control groups received vehicle (intralipid, water or saline). Treatments were evaluated and expressed as % ILS (increased life span over controls). The treatment was evaluated and expressed as the percentage survival at 42 days.

TABLE 1

| Protocol | compound | molecular weight | $IC_{50}$ |
|---|---|---|---|
| P338/0 | 10-Hydroxy-camptothecin | 364 | 139 nM |
| P338/0 | Example 1 compound | 37,808 | 55 nM |

As indicated, the tested composition was given daily [intra-peritoneal (i.p.)×5], twenty-four hours following an injection of P388/0 cells into the abdominal cavity with survival monitored for 42 days.

Discussion

In addition to the increased water solubility provided by the formulations of the present invention, the data indicates that the PEG-prodrug compounds are more efficacious and less toxic than parent compounds. The data of Table 2, below, confirms that PEG-40k-ester of 10-hydroxy CPT provides a significant improvement in survival in the leukemia cell containing mice, compared to controls treated with non-derivitized 10-hydroxycamptothecin. While Applicants are not bound by theory, it is believed that the unique combination of higher molecular weight polymer and the controlled rate of hydrolysis of the particular ester linkages, allow therapeutically effective amounts of the parent compound (e.g., medicament) to be generated before the prodrug is cleared from the body.

TABLE 2

| | | | Results | | | |
|---|---|---|---|---|---|---|
| Test Article | Dose[a]/ (mg/kg) | Total Dose (mg/kg) | Mean time to death[b] (Mean ± Std) | T/C | ILS (%)[c] | % survivors at day 42 |
| Control | — | — | 9.3 ± 0.5 | — | — | 0% |
| PEG-40k-ester of 10-hydroxy CPT | 3.2 | 16 | 25.4 ± 2.6* | 2.7 | 173 | 10% |
| Topotecan | 3.2 | 16 | 17.9 ± 0.5* | 1.9 | 92 | 0% |

[a]Equivalent dose of camptothecin, mice dosed days 1–5.
[b]Kaplan-Meier estimates with survivors censored.
[c]Increased life span (ILS) is (T/C − 1) × 100, where T/C is survival of the tested divided by the survival of the control group
*significant (P < 0.05) compared to control (untreated).
†significant (P < 0.05) compared to Topotecan.

The various publications, patents, patent applications and published applications mentioned in this application are hereby incorporated by reference herein.

While there have been described what are presently believed to be the preferred embodiments of the invention, those skilled in the art will realize that changes and modifications may be made without departing from the spirit of the invention. It is intended to claim all such changes and modifications as fall within the true scope of the invention.

We claim:

1. A polymeric ester of an aromatic, hydroxyl-containing compound, comprising the formula:

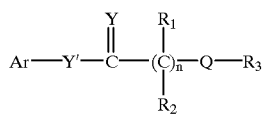

(I)

wherein:
- Ar is a residue of an aromatic, hydroxyl-containing compound;
- Q is a moiety containing a free electron pair positioned three to six atoms from Y';
- Y and Y' are independently O or S;
- $R_1$ and $R_2$ are independently selected from the group consisting of H, $C_{1-6}$ alkyls, aryls, substituted aryls, aralkyls, heteroalkyls, substituted heteroalkyls and substituted $C_{1-6}$ alkyls;
- (n) is zero or a positive integer; and
- $R_3$ is a substantially non-antigenic polymer.

2. The compound of claim 1, wherein $R_3$ further comprises a capping group Z.

3. The compound of claim 2, wherein Z is selected from the group consisting of H, $CO_2H$, $C_{1-6}$ alkyl moieties, dialkyl acyl urea alkyls and

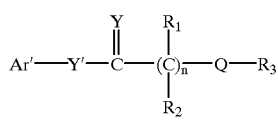

(II)

wherein Ar' is selected form the group consisting of Ar, H and biologically active compound residues.

4. The compound of claim 1, wherein $R_1$ and $R_2$ are independently selected from the group consisting of H, methyl and ethyl.

5. The compound of claim 1, wherein said substituted $C_{1-6}$ alkyl is selected from the group consisting of carboxyalkyls, aminoalkyls, dialkylaminos, hydroxyalkyls and mercaptoalkyls.

6. The compound of claim 1, wherein Q is selected from the group consisting of $C_{2-4}$ alkyls, cycloalkyls, aryls, aralkyl groups substituted with a member of the group consisting of NH, O and S.

7. The compound of claim 6, wherein Q is selected from the group consisting of —$CH_2$—C(O)—N(H)—, and ortho-substituted phenyls.

8. The compound of claim 1, wherein (n) is an integer from 1 to about 12.

9. The compound of claim 8, wherein (n) is 1 or 2.

10. The compound of claim 1, wherein Y and Y' are O.

11. The compound of claim 1, wherein $R_3$ comprises a polyalkylene oxide.

12. The compound of claim 11, wherein said polyalkylene oxide comprises polyethylene glycol.

13. The compound of claim 11 wherein said polyalkylene oxide has a molecular weight of from about 20,000 to about 80,000.

14. The compound of claim 13, wherein said polyalkylene oxide has a molecular weight of from about 25,000 to about 45,000.

15. The compound of claim 14, wherein said polyalkylene oxide has a molecular weight of from about 30,000 to about 42,000.

16. The compound of claim 1, wherein $R_3$ is selected from the group consisting of:
—C(=Y)—$(CH_2)_n$—O—$(CH_2CH_2O)_x$—Z,
—C(=Y)—Y—$(CH_2)_n$—O—$(CH_2CH_2O)_x$—Z,
—C(=Y)—$NR_1$—$(CH_2)_n$—O—$(CH_2CH_2O)_x$—Z,
—$CR_1R_2$—O—$(CH_2)_n$—O—$(CH_2CH_2O)_x$—Z
wherein
- $R_1$ and $R_2$ are independently selected from the group consisting of H, $C_{1-6}$ alkyls, aryls, substituted aryls, aralkyls, heteroalkyls, substituted heteroalkyls and substituted $C_{1-6}$ alkyls;
- (n) is zero or a positive integer;
- Y is O or S;
- Z is a capping group; and
- (x) represents the degree of polymerization.

17. A compound of claim 1 selected from the group consisting of:

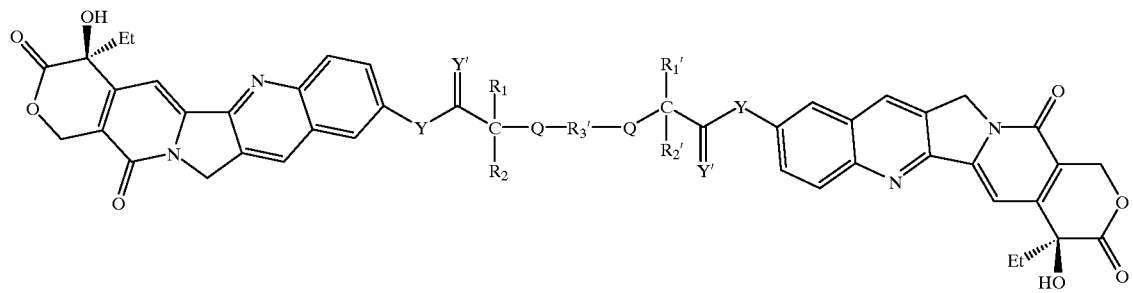

and

-continued

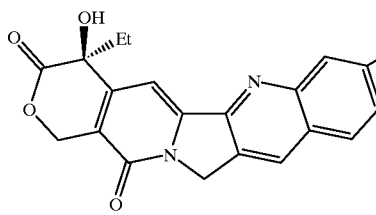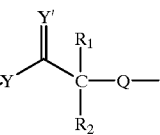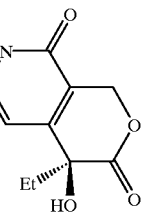

wherein $R_1$ and $R_2$ are independently H or $CH_3$;

$R'_3$ is a bifunctional linking moiety; and

Y and Y' are independently O or S.

18. The compound of claim 1, wherein Ar is a residue derived from the group consisting of 10-hydroxycamptothecin, 11-hydroxycamptothecin, 10,11-dihydroxycamptothecin, etoposide, hydroxyquinolines, parahydroxyanaline mustards, tetracyclines, anthracyclines and combrethastatin.

19. The compound of claim 1 wherein Ar is a residue of an aromatic, hydroxyl containing compound selected from the group consisting of cardiovascular agents, antineoplastics, anti-infectives, anti-fungals, anti-anxiety agents, gastrointestinal agents, central nervous system-activating agents, analgesics, fertility agents, contraceptive agents, anti-inflammatory agents, steroidal agents, anti-urecemic agents, vasodilating agents, and vasoconstricting agents.

20. A compound of claim 3 having the formula

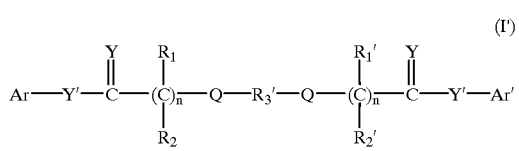

(I')

wherein $R_3'$ is a bifunctional linker moiety; and $R_1'$ and $R_2'$ are the same as $R_1$ and $R_2$ or another member of the group defined for $R_1$ and $R_2$ respectively.

21. A method for preparing a conjugate of an aromatic, hydroxyl-containing compound, comprising, reacting an aromatic, hydroxyl-containing compound with an acid derivative of a bifunctional linking compound in the presence of an acid chloride derivative of a phenyl phosphonic acid.

22. The method of claim 21, wherein said derivative of said phenyl phosphonic acid is an aryl dihalophosphate.

23. The method of claim 22, wherein said acid derivative of said bifunctional linking compound comprises a substantially non-antigenic polymer.

24. The method of claim 23, wherein said acid derivative of said substantially non-antigenic polymer has the structure:

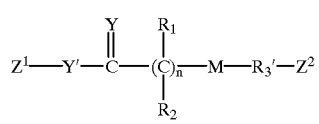

(IV)

M is X or Q;

X is an electron withdrawing group;

Q is a moiety containing a free electron pair positioned three to six atoms from Y'

$R_1$ and $R_2$ are independently selected from the group consisting of H, $C_{1-6}$ alkyls, aryls, substituted aryls, aralkyls, heteroalkyls, substituted heteroalkyls and substituted $C_{1-6}$ alkyls;

$R_3'$ is a bifunctional linking moiety;

Y and Y' are independently O or S;

(n) is zero or a positive integer;

$Z^1$ and $Z^2$ are independently $CO_2R_4$, $OR_5$, $COR_6$, H, or a $C_{1-4}$ alkyl, branched or substituted alkyl;

$R_4$ is an N-succinimidyl, an N-benzotriazolyl or an acid activating group;

$R_5$ is $R_1$ or C(=O)-halogen, para nitrophenyl carbonate, imidazolyl carbonate, or N-hydroxysuccinimidyl carbonate; and $R_6$ is a thiazolidinyl thione, imidazolyl or acid activating group.

25. The method of claim 22, wherein said aryl dihalophosphate is phenyl dichlorophosphate.

26. The method of claim 23, wherein said acid derivative of said substantially non-antigenic polymer comprises a polyalkylene oxide.

27. The method of claim 26, wherein said polyalkylene oxide has a molecular weight of from about 20,000 to about 80,000.

28. A method of treating a mammal with prodrugs, comprising:

administering to a mammal in need of such treatment an effective amount of a composition of claim 1.

29. The method of claim 24, wherein (n) is an integer from 1 to about 12.

30. The method of claim 29, wherein (n) is 1 or 2.

31. The method of claim 24, wherein X is selected from the group consisting of O and $NR_1$.

32. The method of claim 24, wherein Q is selected from the group consisting of $C_{2-4}$ alkyls, cycloalkyls, aryls, aralkyl groups substituted with a member of the group consisting of NH, O and S.

33. The method of claim 24, wherein Q is selected from the group consisting of —$CH_2$—C(O)—N(H)—, and ortho-substituted phenyls.

34. The compound of claim 20, wherein $R_3'$ is a residue of a substantially non-antigenic polymer.

35. The compound of claim 34 wherein said substantially non-antigenic polymer has a molecular weight of about 20,000 or greater.

36. The compound of claim 19 wherein Ar is a residue of an aromatic, hydroxyl containing compound that is an anticancer agent.

37. The compound of claim 19 wherein Ar is a residue of an aromatic, hydroxyl containing compound that is selected from the group consisting of topotecan, SN-38, camptothecin derivatives, nitrogen mustard derivatives, tetracyclic pharmaceuticals, quinolone antibiotics.

38. The compound of claim 37 wherein Ar is a residue of an aromatic, hydroxyl containing compound that is selected from the group consisting of 7-ethyl-10-hydroxycamptothecin, 7-alkyl-10-hydroxycamptothecins; etoposide, parahydroxyaniline mustard, doxycycline, anthracyclines, and combretastatin.

39. The method of claim 28 wherein said mammal is in need of anticancer treatment.

40. The method of claim 28 wherein said mammal is treated with an effective amount of a compound according to claim 37.

41. The method of claim 28 wherein said mammal is treated with an effective amount of a compound according to claim 38.

42. The method of claim 28 wherein said mammal is a human.

* * * * *

UNITED STATES PATENT AND TRADEMARK OFFICE
CERTIFICATE OF CORRECTION

PATENT NO. : 6,011,042
DATED : January 4, 2000
INVENTOR(S) : Greenwald, R.B. et al.

It is certified that error appears in the above-identified patent and that said Letters Patent is hereby corrected as shown below:

Column 10,
Lines 38-48, the formula should appear as follows:

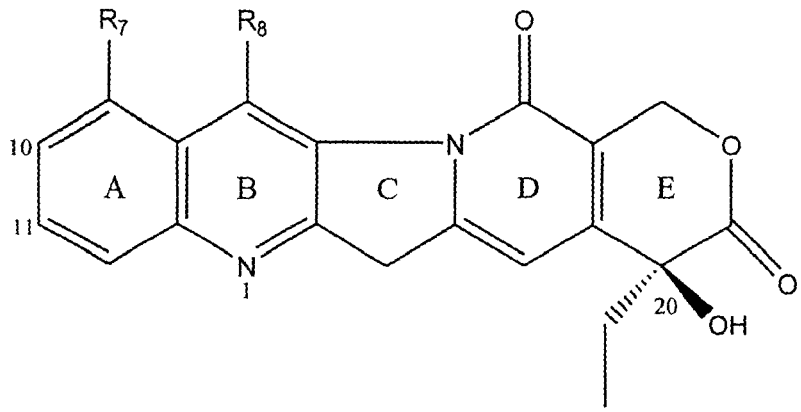

Signed and Sealed this

Thirty-first Day of January, 2006

JON W. DUDAS
*Director of the United States Patent and Trademark Office*